United States Patent [19]

Ray et al.

[11] Patent Number: 4,904,260

[45] Date of Patent: * Feb. 27, 1990

[54] PROSTHETIC DISC CONTAINING THERAPEUTIC MATERIAL

[75] Inventors: Charles D. Ray, Wayzata; Terry P. Corbin, Golden Valley, both of Minn.

[73] Assignee: Cedar Surgical, Inc., Minnetonka, Minn.

[ * ] Notice: The portion of the term of this patent subsequent to Sep. 20, 2005 has been disclaimed.

[21] Appl. No.: 223,400

[22] Filed: Jul. 25, 1988

Related U.S. Application Data

[63] Continuation-in-part of Ser. No. 87,424, Aug. 20, 1987, Pat. No. 4,772,287.

[51] Int. Cl.$^4$ .......................... A61F 2/44; A61M 31/00
[52] U.S. Cl. ........................................... 623/17; 623/12; 604/891.1; 604/131; 424/424; 424/DIG. 7
[58] Field of Search .............. 604/93, 131, 175, 891.1, 604/892.1; 623/7, 8, 16, 17, 66, 11, 12; 128/69, 92 YM; 424/422–426, DIG. 7; 530/353–365

[56] References Cited

U.S. PATENT DOCUMENTS

| 3,855,638 | 12/1974 | Pilliar | 623/16 |
| 3,934,274 | 1/1976 | Hartley, Jr. | 623/8 |
| 3,948,254 | 4/1976 | Zaffaroni | 623/66 X |
| 3,987,790 | 10/1976 | Eckenhoff et al. | 604/892.1 |
| 4,367,741 | 1/1983 | Michaels | 604/822.1 |
| 4,485,096 | 11/1984 | Bell | 623/16 X |
| 4,772,287 | 9/1988 | Ray et al. | 623/17 |

FOREIGN PATENT DOCUMENTS 0895433 1/1982 U.S.S.R. .................. 623/17

OTHER PUBLICATIONS

Hawley's Condensed Chemical Dictionary, Eleventh Edition, Van Nostrand Reinhold Co., 1987, p. 610.

Primary Examiner—Richard J. Apley
Assistant Examiner—David J. Bender
Attorney, Agent, or Firm—Moore & Hansen

[57] ABSTRACT

By implanting two prosthetic disc capsules side-by-side into a damaged disc of a human spine, both height and motion, including front-to-back bending, can be maintained. Each prosthetic disc capsule has a bladder enclosing a fluid containing a therapeutic material that is slowly diffusible through a semi-permeable membrane of the bladder. The fluid filling the semi-permeable membrane preferably is an aqueous solution that has gel-like properties that afford a viscosity and velocity-shear behavior imitating the natural rheology of intradiscal nuclear tissue. Those properties are obtained when the aqueous solution is of a mucopolysaccharide such as hyaluronic acid or soldium hyaluronate.

17 Claims, 2 Drawing Sheets

PROSTHETIC DISC CONTAINING THERAPEUTIC MATERIAL

CROSS-REFERENCE TO RELATED APPLICATION

This application is a continuation-in-part of copending application Ser. No. 07/087,424, filed Aug. 20, 1987 (now U.S. Pat. No. 4,772,287, issued Sept. 20, 1988), that claims an elongated, cylindrical, prosthetic, intervertebral disc capsule having an outer layer of strong, inert fibers intermingled with a bioresorbable material which attracts tissue ingrowth and surrounds a fluid-filled bladder. The fluid preferably is a thixotropic gel having a viscosity and velocity-shear behavior imitating the natural rheology of intradiscal nuclear tissue. The copending application also claims a simple surgical procedure for implanting a pair of the capsules to repair a degenerated disc.

BACKGROUND ART

1. Field of the Invention

The present invention concerns a prosthetic disc that can be identical to the capsule claimed in the above-cited application, except for modifications in the fluid-filled bladder and its fluid. Like the discs of that application, a pair of the novel discs can be implanted to repair a degenerated disc of the spine of a vertebrate, especially the spine of a human being.

2. Description of Related Art

The normal intervertebral disc has an outer ligamentous ring called the anulus which inds the adjacent vertebrae together and is constituted of collagen fibers that are attached to the vertebrae and cross each other so that half of the individual fibers will tighten as the vertebrae are rotated in either direction, thus resisting twisting or torsional motion. Torsional movement between vertebral segments is further restricted by the facet joints.

Deep inside the anulus lies a nucleus pulposis of loose tissue which is slippery and slimy (having about 85% water content) and moves about during bending from front to back or from side to side. Thus, as the opposing surfaces of the vertebrae alter their parallel relationship to each other with bending, the nuclear tissue moves about to fill up the change in distance (wedging) that occurs in the opposing ends of the disc space. With bending, the anulus will bulge on the downward wedged side and be stretched tightly on the upward wedged side.

A classical disc herniation occurs when the anular fibers are weakened or torn and the inner tissue of the nucleus becomes permanently bulged, distended, or extruded out of its normal anular confines. Leg pain in such cases results from this nuclear tissue (or an intact, weakened, bulging anulus) compressing a nerve which passes outward from the spinal canal to the leg.

A major cause of persistent, disabling back pain takes place when the anulus becomes chronically inflamed by a degenerative process. Small nerves that come from branches encircling the outside of the anulus penetrate for a short distance (perhaps 6 to 8 mm) into the anular fibers. Constant abnormal motion between the fiber layers of the anulus, due to loss of bonding between them, may stretch and grind the tiny pain fiber nerve endings. Thus the patient becomes sensitive to the slightest movement. These cases require some form of mechanical limitation to intervertebral disc motion at the painful segment. For the most persistent cases, bony fusions are often performed to stop the painful motion by permanently locking the vertebrae together. In many cases it may be preferred to allow some minor movement (less than that which causes the pain). Preserving some movement helps to prevent mechanical breakdown at nearby segments. At present, to attempt to make and maintain these flexible fusions is not reliably feasible.

Whenever the nuclear tissue is herniated or removed by surgery, the disc space will narrow and lose much of its mobility. Considering that rotation is potentially destructive to the anulus and nucleus, rotation should be limited by any prosthetic device to replace the removed, herniated or degenerated disc, preferably while allowing bending, especially forward and backward. Lateral bending is of lesser importance.

Although we are not aware of any means currently being used to preserve both the height of the disc space and important motions of the vertebral segment, a number of patents describe prosthetic discs that are said to be useful for those purposes. For example, U.S. Pat. No. 3,875,595 (Froning) shows a prosthesis shaped to replace the entire nucleus pulposis of an intervertebral disc. Froning's "prosthesis is a hollow, flexible bladder-like member which is filled with a fluid and/or plastic under adjustable pressure. The pressure may be increased or decreased while the prosthesis is in place over a period of time to determine by trial and error the optimum pressure, and thereupon the stem of the prosthesis is removed. The optimum pressure is maintained over an indefinite period of time by providing an inflating fluid or plastic having properties for holding fluid or water under pressure normally occurring within the disc sufficient to avoid depletion of the inflating contents, a feature which would duplicate the feature of the normal disc" (col. 1, lines 30–43). Froning's prosthesis has stud-like protrusions which fit into sockets that have been forced through the bony end plates of the adjacent vertebrae to anchor the prosthesis against slippage.

U.S. Pat. No. 4,349,921 (Kuntz) shows an intervertebral disc prosthesis formed from any biologically acceptable material such as high density polyethylene, polymethacrylate, stainless steel, or chrome cobalt alloy and dimensionally shaped to replace a natural disc. One of the longitudinal ends of the prosthesis can have a raised flange to facilitate handling and to prevent penetration to an excessive depth, while the other longitudinal end is wedge-shaped to facilitate insertion. The superior and inferior faces are provided with surface characteristics such as grooves, corrugations, or projections to produce a "friction-fit" and are convex to correspond to the adjacent vertebral surfaces.

U.S. Pat. No. 3,867,728 (Stubstad et al.) shows intervertebral disc prostheses of a variety of constructions. Each of these prostheses has a core made of elastic polymer, e.g., a reinforced resilient block of elastomer such as silicone rubber or polyurethane, and a covering providing an outer surface of an open-pore tissue-ingrowth-receptive material. While most of the illustrated prostheses are single elements of a shape approximating that of a human disc, "another version includes a plurality of flexible, curved, bar-like elements with configurations which allow them to lie side by side so as to occupy the interior space of a natural disc from which the nucleus pulposus has been removed" (penultimate sentence of Abstract). See FIGS. 23 and 24. To repair a ruptured disc with either a single or a multi-element prosthesis, the interlaminar space is posterlorly exposed and "laminectomy is performed to gain better access to the disc space and to provide an opening . . . through which the nucleus pulposus will be removed and the prosthesis inserted. The spinal dura and nerve root are identified, the root is dissected free, and together these are retracted laterally to expose the herniation" (col. 14, lines 17-27). After cleaning out the ruptured disc to create a space to receive the prosthesis, "the end plate that will be adjacent to the ingrowth surface of the prosthesis is scraped clean of loose tissue and left with a bleeding surface to promote fixation of the prosthesis by tissue ingrowth" (col. 14, lines 35-39). If the two-element prosthesis is used, "The two segments may be further stabilized by tying them together by cords 129 or by suturing to one of the adjacent vertebrae or other available tissue" (col. 14, lines 48-50).

Intervertebral disc prostheses which are mechanically fastened between vertebrae are shown in U.S. Pat. No. 4,554,914 (Kapp et al.); No. 4,309,777 (Patil); No. 3,426,364 (Lumb); and No. 4,636,217 (Ogilvie et al.).

Vascular circulation and nerve supply to the disc is limited to the outer layers of the anulus, never penetrating more than several millimeters. Most of the nutrition to the inner anulus and nucleus is provided by diffusion throughthe end plates of the vertebral bodies, these bones being quite vascular. Thus, the central disc is the largest avascular and non-innervated structure of the body. A variety of degenerative changes may occur if the vertebral end plates become sclerotic (hardened). Nutrition to the inner disc slowly ceases, resulting in nuclear and anular fiber degeneration, shrinkage of the nucleus, segmental laxity, spur formation, disc space collapse, spontaneous fusion, and other changes.

The physiological isolation of the central disc is normally so complete, relative to circulating body fluids and chemicals, that throughout lifetime, provided the disc remains intact, protein fractions, enzymes and other compounds peculiar only to the inner disc are never exposed to the rest of the body constituents. As a result, when the disc anulus is torn, hidden internal discal constituents may suddenly become exposed to the general circulation. In many cases, antigen-antibody reactions may thus begin, as the circulating immune system is exposed to new, "foreign" tissues. Frank allergic reactions to autologous disc tissue have been documented in controlled animal experiments.

A further situation of greater importance may also occur, namely, a combined, chronic mechanical and chemical irritation of the fine free nerve endings found in the outer disc layers. Anular cracks permit nuclear materials to reach these nerve endings; shearing forces between delaminating layers of anular fibers irritate the traversing, penetrating free nerve endings. These irritations lead to mechanically induced acute, and postural, chronic pain perception arising from the outer rind of the disc. Since the anterior one-third of the disc in inervated by deep sympathetic fibers and the posterior two-thirds by somatic sensory fibers, the combined circular irritation produces a highly disagreeable and often disabling pain. At the present time, the primary treatment for such common pain is (a) alteration of life style, (b) reduction in overall activity level, (c) extensive exercise program, (d) use of antiinflammatory medication, (e) surgical or enzymatic discectomy, or (f) stoppage of mechanical motion by bony fusion.

SUMMARY OF THE INVENTION

The invention provides an elongated, cylindrical prosthetic intervertebral disc capsule having a diameter approximating the height of a human disc space and a length approaching the sagittal diameter of the vertebral body, which capsule includes a flexible bladder which is chemically and biologically inert and comprises a semi-permeable membrane enclosing a fluid containing a therapeutic material that is slowly diffusible through the semi-permeable membrane, and a layer of strong fibers encompassing the fluid-filled membrane. Among useful therapeutic materials are hormones, neurotransmitter peptides, anitinflammatory substances, neurotropic factors, and other materials that would serve to reduce inflammation, reduce pain, incite repair of the anular fibers or nuclear tissue, or have some other therapeutic function.

Clinical investigation has clearly shown that when quantities (as little as 0.1 milliliters) of local anesthetic (e.g., 1% lidocaine) are injected inside the nucleus of a mechanically painful, highly sensitive disc, the pain will usually cease in less than 10 seconds and will be completely relieved for several hours thereafter. In such cases, the degenerative changes of the disc space are not particularly important, per se, but the disabling pain demands some such treatment.

By incorporating long-acting anesthetics such as lidocaine or bupivacaine into the fluid of the bladder, their gradual permeation through the semi-permeable membrane should hold the free nerve endings in a state of depolarization, thereby inhibiting painful discharges. By incorporating into the fluid depository steroids such as methylprednisolone or dexamethasone, their gradual permeation through the semi-permeable membrane should reduce the release of arachidonic acid and histamine by mast cells, both of which would otherwise trigger firings of the pain receptor free nerve endings. An entirely opposite approach is also feasible, that is, to promote the destruction of free nerve endings and sympathetic terminals so that these pain receptors are eliminated from delaminated, mechanically unstable anular layers. For example, the fluid of the prosthetic capsule can include 6-hydroxydopamine (which destroys adrenergic nerve endings) or vinblastine (which blocks axonal transport), both of which cause death and tropic retreat of sensory and sympathetic fibers.

Other therapeutic agents that can be incorporated into the fluid of the bladder include nerve growth factor (NGF) such as a polypeptide that can promote nerve repair and prevent nerve cell death. This material, effective in nanogram concentrations, is now being produced by bacterial gene splicing and cloning techniques. Other therapeutic agents include epidermal growth factor which can produce a transformation of recipient cells leading to the replacement of key tissues such as torn anular fibers.

The semi-permeable membrane of the bladder of the novel prosthetic disc capsule should be flexible as well as chemically and biologically inert, e.g., a microporous organic film such as microporous polytetrafluoroethylene (marketed as "Gore-Tex") or a tightly woven fabric of oriented poly(ethylene terephthalate) fibers that has been plasma-deposited with polytetrafluoroethylene (marketed as "Plasma TFE" by Atrium Medical Corp., Hollis, NH). The pore size of the semi-permeable membrane should be sufficiently small to block the passage of human cells. Because the smallest cells of the human body are red blood cells about 7 micrometers in diameter, the pore size preferably is less than 7 micrometers. Although red blood cells would be trapped in somewhat larger pores, this would tend to log the pores, eventually rendering them useless. A pore size on the order of 1–7 micrometers permits almost every useful therapeutic agent to pass.

The bladder may also comprise impermeable organic film which likewise should be flexible. Suitable impermeable organic films include oriented poly(ethylene terephthalate), high-density polypropylene, silicone rubber, and copolymers of silicone and carbonate, all of which are chemically and biologically inert.

Both "Gore-Tex" and "Plasma TFE" semi-permeable membranes are marketed as a tube, the diameter of which approximates the thickness of a human disc. One of these tubes can be cut to a length approximating the sagittal diameter of the vertebral body, and its ends can be closed by being fused to circles of an impermeable organic film. The fusing can be carried out by heat sealing or ultrasonically. In order to form the capsule illustrated in FIG. 1 of the drawing, one of the circles of impermeable film can in turn be fused to a tube of the same impermeable material.

The fluid enclosed in the bladder preferably is a thixotropic gel having a viscosity and velocity-shear behavior imitating the natural rheology of intradiscal nuclear tissue. The thixotropic gel may be a mixture of an inorgnic oil (e.g., silicone or fluorocarbon) and a gelling agent such as fumed silica (preferably providing from approximately 3 to 10% by weight of the mixtue and affording a Brookfield viscosity between 100 and 10,000 cps. at 6 rpm). The viscosity of the fluid is selected to permit movement with normal rapidity during bending at the intervertebral space while restricting motion, especially during slow postural changes. A bulletin entitled "Cab-O-Sil Properties and Functions" from Cabot Corp. (dated 9/83) says at page 10 that "Cab-O-Sil" fumed silica has been authorized by F.D.A. for use in pharmaceutical products for internal and topical applications.

Preferably, the thixotropic gel in the bladder is aqueous such as an aqueous solution of a mucopolysaccharide such as hyaluronic acid or sodium hyaluronate, both of which have elastic and gel-like properties and naturally occur in the human body. When containing such a gel-like solution, the bladder acts like a natural human disc. It can relieve pressure by allowing water to be squeezed out through its semi-permeable membrane, and because the solution is hydrophilic, the bladder can rejuvenate itself by slowly recovering water from the patient's body.

The outer layer of the novel capsule preferably is made of strong, inert fibers intermingled with a bioresorbable (or bioabsorbable) material which attracts tissue ingrowth. Those fibers, as well as fiber of other elements of the novel disc capsule, can be made of carbon or a polymer, including either natural or synthetic polymers such as cold-drawn poly(ethylene terephthalate) polyester fibers. The bioresorbable material can be polylactic or polyglycolic acid or collagen (e.g., semisynthetic), each of which normally becomes replaced by tissue ingrowth and thus becomes bonded to surrounding tissue. This replacement by living tissue assures the permanent flexibility of the implanted prosthesis. See U.S. Pat. No. 4,643,734 (Lin) which names additional useful bioresorbable materials.

The bioresorbable material may itself be fibrous and interwoven with the inert fibers. On the other hand, the outer layer, circumferential flanges, and longitudinal vanes can be woven together of inert fibers (either coated or uncoated with bioresorbable material) and then impregnated with bioresorbable material.

After implantation, it is not necessary that there be an ingrowth of vertebral body bone into the outer layer of the prosthetic disc capsule so long as a close fibrous bond develops between the outer layer and the bone. The fibers of the outer layer preferably are woven to permit considerable pressure containment.

The prosthetic disc capsules should be implanted in pairs. A surgical procedure for their implantation (that is claimed in the above-cited pending application) includes the steps of (1) jacking apart the vertebrae adjacent to a damaged disc, (2) forming a substantially sagittal bore in the damaged disc near each of its lateral edges and spaced from the other bore, and (3) inserting an elongated cylindrical prosthetic disc capsule axially into each bore.

When two of these capsules have been inserted side-by-side into the nucleus of the anulus of a damaged disc, each lying near one of the lateral edges of the disc, they will maintain both height and motion, including front-to-back bending, at the disc space, but will limit rotation, translocation and, to a lesser degree, bending from side to side.

The preferred posterior surgical approach involves drilling an 11-mm hole to provide a window through each of the facet joints, either before or after step (1) of the above-outlined surgical procedure. Then using the windows for access, the surgeon performs step (2) of the procedure and removes debris from the boring and any other unwanted material of the nucleus of the damaged disc. Then in step (3), a prosthetic disc capsule is inserted through each of the windows into the bore. In some cases, the implanted disc capsules can reestablish disc height, an especially desirable objective in massively herniated discs or those that have continued to shrink following a much earlier herniation.

The bores drilled in the disc preferably are sufficiently large to slightly decorticate the end plates of the adjacent vertebrae, thus promoting the attachment of the prosthetic capsules to the bone and adjacent tissue.

In the foregoing posterior approach, the bores inherently are angulated toward each other at about 5°–10° off true sagittal, and this provides the advantage of permitting the bore to be deeper before there is any danger of the drill bit emerging from the other side of the disc. Because that angle is quite small, the implanted prosthetic capsules act virtually as if their axes or elongated directions were positioned in the true sagittal direction.

Drilling of the facet joints can be avoided either by an anterior approach or by accessing the damaged disc posteriorly, medial to the facet joints. The latter approach involves the hazard of moving and thus possibly damaging the spinal nerves. Furthermore, this would require the bores in the disc to extend in the sagittal direction or slightly divergent from sagittal, so that the bores would need to be shorter than when drilling through facet windows. On the other hand a posterior approach medial to the facet joints may be feasible by a percutaneous technique in which the prosthetic disc capsules are moved into position with a minimum of disruption.

When the prosthetic capsule is connected to a remote chamber that is designed to be punctured by a hypodermic needle, the chamber should be placed to be easily approachable by a long needle under x-ray fluoroscopic control. If an implanted prosthetic disc capsule causes some remolding of the vertebral body bone, then the space height will decline, and reinflation may be used to restore the height, perhaps several times. Thixotropic gels of differing behavior may be required in various patients, and the ability to modify the gel after the prosthetic capsule has been implanted is permitted by a chambe which affords remote access to the cavity of the bladder.

When the bladder of the novel prosthetic disc capsule is connected by tubing to a remote reservoir or chamber which is needle-puncturable, the bladder need not be filled with fluid until after being inserted into the damaged disc. After the novel disc capsule has been inserted into a damaged disc, a hypodermic needle can be used to inject fluid into the chamber, thus forcing the fluid through the tubing into the bladder and inflating the bladder. The bladder may thus be fully inflated immediately after its insertion, or it may be inflated a little at a time in order to adjust or slowly increase the height of the disc space. A slow restoration of the disc height would permit natural elatic recovery, whereas a sudden rise might further disrupt or tear the anulus of the disc. The chamber can also be used with a hypodermic needle to withdraw some of the gel if it is judged to be overinflated.

When the chamber is needle-puncturable, it can also be used to add to or withdraw from the bladder different therapeutic agents.

The chamber need not be needle-puncturable when it is separated into two components by a flexible, impermeable film. One of those compartments communicates with the bladder and contains a fluid such as a thixotropic gel while the other compartment may contain a hygroscopic material and is formed with a moisture-permeable wall. Moisture of the body causes a gradual swelling of the hygroscopic material, hence forcing a gradual flow of thixotropic material to inflate the bladder gradually.

In order to limit lateral bulging of the prosthetic disc capsule while in the disc space, strong, inert fibers may be woven into the outer layer to extend transversely through the blader. These transverse fibers can be identical to the strong, inert fibers of the outer layer. When the prosthetic disc capsule is further inflated from a remote chamber, the transverse fibers will result primarily in an increase in the disc height.

The ends of the novel prosthetic disc capsules may be invaginated so that as internal pressure rises or falls with vertebral loading, the ends may invert or evert, exerting pressure against surrounding tissue. This means to permit flexibility of the prosthetic disc capsule does not require an elastic stretch and recoil of the structure.

To guard against the possibility that one of the prosthetic disc capsules may tend to work itself out, each of the capsules may be provided with circumferential flanges, like collars, formed to make the capsule easy to insert but more difficult to extract or to be spontaneously expelled.

To guard against the possibility of the capsule rotating in the space during insertion or after implantation, the capsule preferably is provided with longitudinal fins or vanes. Both such longitudinal vanes and circumferential flanges can be formed of strong, inert fibers which can be identical to the fibers of the outer layer.

When the novel prosthetic disc capsule includes a remote chamber, the chamber, connecting tubing, and part of the bladder preferably are formed of the same material, e.g., by blow molding. When the cylindrical portion of the badder is a semi-permeable membrane, a needle can be used to pull the transverse fibers through the membrane and also to interweave them with fibers of the outer layer, preferably while simultaneously weaving the outer layer and its ridges and flanges.

BRIEF DESCRIPTION OF THE DRAWINGS

In the drawing, all figures of which are schematic.

DESCRIPTION OF THE PREFERRED EMBODIMENT

Figure 1:
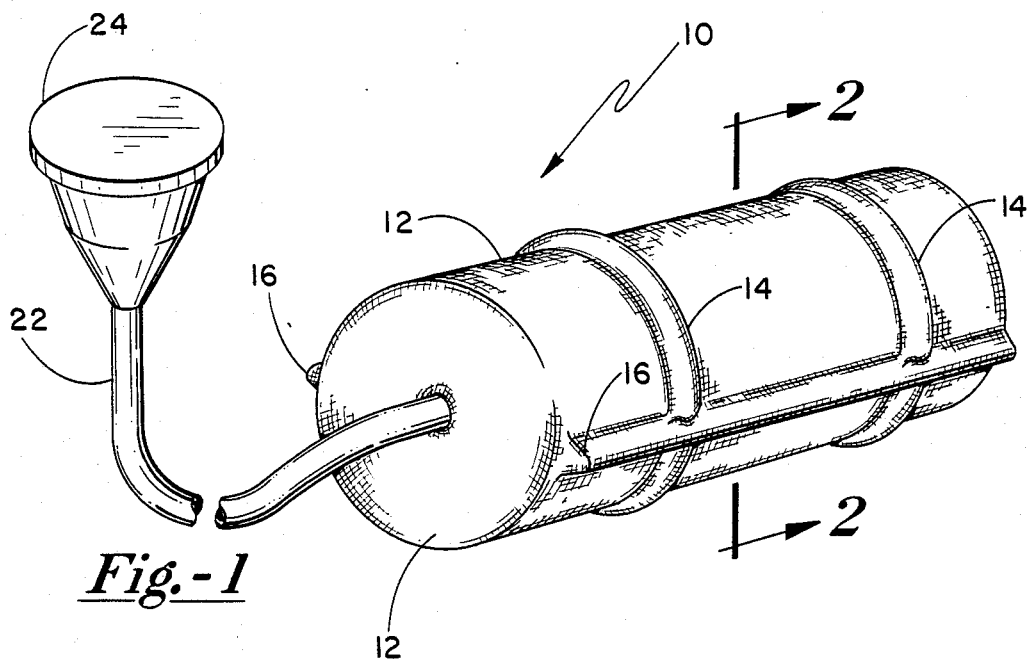
FIG. 1 is a perspective view of a preferred elongated prosthetic disc capsule of the invention with a remote chamber by which the capsule can be further inflated or deflated.

The elongated prosthetic disc capsule 10 shown in FIG. 1 has an outer layer 12 consisting of a network of strong, inert polymeric fibers interwoven with bioresorbable fibers which attract tissue ingrowth. Also interwoven with said fibers are strong, inert polymeric fibers arranged to form two circumferential bands or flanges 14 and longitudinal fins or vanes 16 that project from the external face of the outer layer 12.

Figure 2:
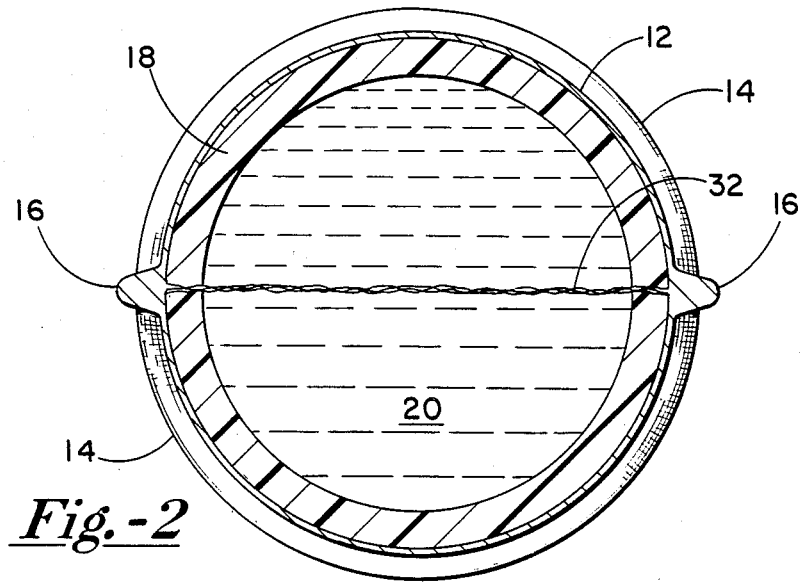
FIG. 2 is an enlarged central section along line 2—2 of FIG. 1.

The outer layer 12 surrounds a bladder 18 that contains a thixotropic gel 20 as seen in FIG. 2, which gel includes one or more therapeutic agents. A small tube 22 connects the bladder to a small remote chamber 24 that is needle-puncturable. After the prosthetic disc capsule 10 has been implanted into a human spine as shown in FIGS. 4 and 5, the tube 22 permits the chamber 24 to be positioned as in FIG. 4 so that thixotropic gel can be added to or drawn out of the chamber 24 by insertion of a hypodermic needle without penetrating into the spinal zone.

Beneath the outer layer 12 of fibers, the cylindrical portion of the bladder 18 is a semi-permeable membrane, and the circular ends are an immpermeable organic film, the edges of which have been ultrasonically sealed to the semi-permeable membrane.

Figure 3:
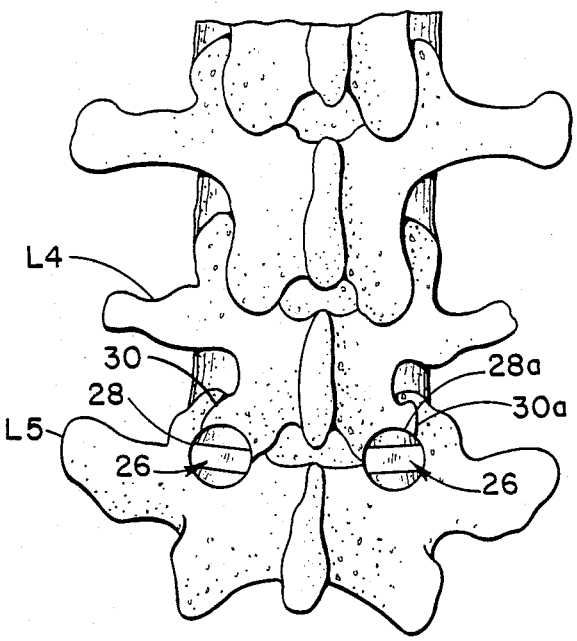
FIG. 3 is a posterior view of a human spine showing two windows that have been drilled through lower portions of facets to provide convenient access for implanting a pair of the prosthetic disc capsules of FIGS. 1 and 2 into a degenerated disc between the L4 and L5 vertebrae.

The zone of implantation is at a degenerated or herniated disc 26 between the L4 and L5 lumbar vertebrae. As seen in FIG. 3, windows 28 and 28a have been drilled into lower portions of the facets 30 and 30a. Using those windows, a pair of bores 31 and 31a have been drilled into the disc 26, with each bore near a lateral edge of the damaged disc 26 and angulated toward the other bore at about 10° to the sagittal direction. Also using those windows, the drilling debris and possibly other parts of the nucleus of the disc have been removed, after which the prosthetic disc capsule 10 and an identical prosthetic disc capsule 10a have been axially inserted into the bores 31 and 31a, respectively, without disturbing the spinal nerve.

Figure 4:
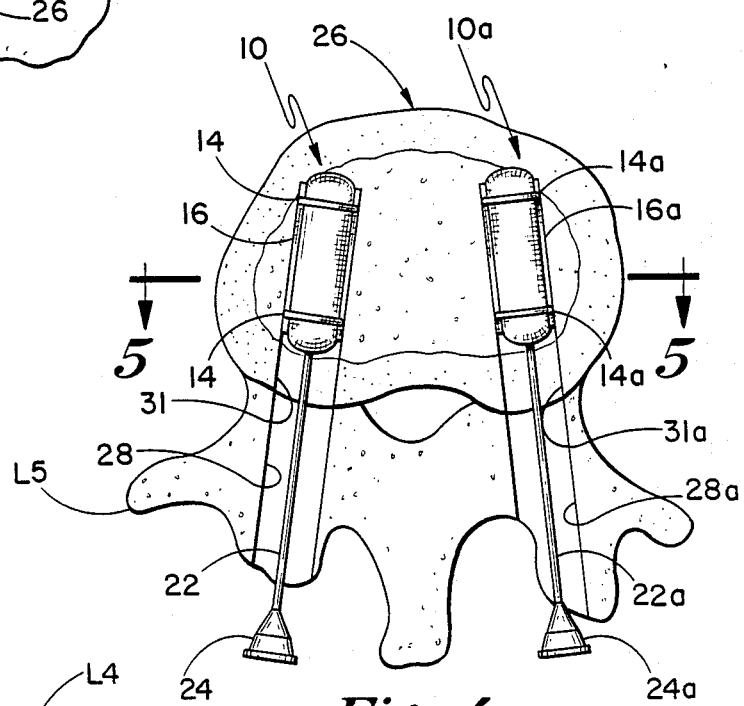
FIG. 4 is a transaxial view of the spine as prepared in FIG. 3 with the L4 vertebra not shown.
Figure 5:
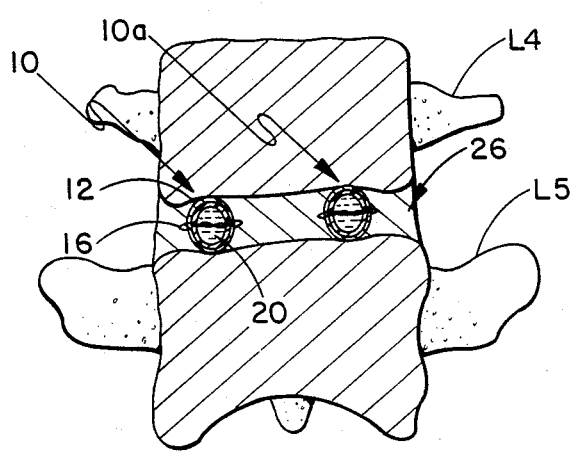
FIG. 5 is a section along line 5—5 of FIG. 4, reduced in size.

As seen in FIG. 4, the prosthetic disc capsules 10 and 10a have been inserted into the bores 31 and 31a and hence are positioned side-by-side and spaced apart with the elongated direction or axis of each of the capsules extending at an angle of about 10° to the sagittal direction. FIG. 5 shows that the prosthetic disc capsules 10 and 10a have restored the height of the space between the vertebrae L4 and L5 with a tightening of the anulus of the disc 26. This relieves pressure on the nerves that had been caused by a combination of collapse of the disc space and bulging of the weakened anulus.

Referring again to FIG. 2, a number of polymeric or other strong, inert fibers 32 extend transversely across the equator of the disc capsule 10 and are interwoven with the fibers of the outer layer 12. Because of these transverse fibers 32, the prosthetic disc capsule 10 resists becoming flattened by vertical pressures in the patient's spine, thus retaining the spacing between the lumbar vertebrae L4 and L5 between which it and the disc capsule 10a are implanted. The longitudinal vanes 16 and 16a serve to inhibit rotation of the prosthetic disc capsules, while the circumferential flanges 14 and 14a better anchor the disc capsules in the space between the vertebrae.

Unlike ordinary implanted devices containing slowly-releasable therapeutic agents, the novel prosthetic disc is primarily a structural element and secondarily a pharmacologically active device. That is, because the damaged disc has already been altered in mechanical behavior, a preservation or restoration of normal mechanical function is the first step to the return of the patient's comfort and mobility. Because the novel prosthetic disc can gradually dispense therapeutic agents into the body, it also is pharmacologically active. No other structure implant is known that is pharmcologically active. Neither is any pharmacologically-active implant known that also has structural functions.

We claim:

1. An elongated cylindrical prosthetic intervertebral disc capsule having a diameter approximating the height of a human disc space and a length approaching the sagittal diameter of the vertebral body, said capsule comprising:
    a flexible bladder which is chemically and biologically inert and comprises a semi-permeable membrane enclosing a fluid containing a therapeutic material that is slowly diffusible through the semi-permeable membrane, and
    a layer of strong fibers encompassing the fluid-filled membrane.

2. A prosthetic disc capsule as defined in claim 1 wherein the semi-permeable membrane is a microporous organic film.

3. A prosthetic disc capsule as defined in claim 2 wherein the microporous organic film is microporous polytetrafluoroethylene.

4. A prosthetic disc capsule as defined in claim 1 wherein the semi-permeable membrane is a tightly woven fabric of oriented poly(ethylene terephthalate) fibers that has been plasma-deposited with polytetrafluoroethylene.

5. A prosthetic disc capsule as defined in claim 1 wherein the pore size of the semi-permeable membrane is sufficiently small to block the passage of human cells.

6. A prosthetic disc capsule as defined in claim 5 wherein the pore size of the semi-permeable membrane is on the order of 1–7 micrometers.

7. A prosthetic disc capsule as defined in claim 1 wherein the bladder also comprises flexible impermeable organic film.

8. A prosthetic disc capsule as defined in claim 7 wherein the semi-permeable membranee is a tube, the diameter of which approximates the thickness of a human disc, and the length of which approximates the sagittal diameter of the vertebral body, and he ends of the tube are sealed to circles of an impermeable organic film.

9. A prosthetic disc capsule as defined in claim 1 wherein the fluid filling the bladder is a gel having a viscosity and velocity-shear behavior imitating the natural rheology of intradiscal nuclear tissue.

10. A prosthetic disc capsule as defined in claim 9 wherein the fluid filling the bladder is an aqueous solution of a mucopolysaccharide.

11. A prosthetic disc capsule as defined in claim 10 wherein the mucopolysaccharide is selected from hyaluronic acid and sodium hyaluronate.

12. A prosthetic disc capsule as defined in claim 1 having strong, inert fibers woven into the outer layer and extending transversely through the semi-permeable membrane to limit lateral bulging.

13. A prosthetic disc capsule as defined in claim 12 wherein a bioresorbable material is intermingled with the inert fibers.

14. A prosthetic disc capsule as defined in claim 13 wherein said bioresorbable material comprises fibers which are interwoven with said inert fibers.

15. A prosthetic disc capsule as defined in claim 13 wherein said bioresorbable material is coated on the inert fibers.

16. A prosthetic disc capsule as defined in claim 1 and including a hollow tubing communicating with the interior of said membrane and an external chamber, and means for injecting or withdrawing fluid into or from the chamber.

17. An elongated cylindrical prosthetic intervertebral disc capsule having a diameter approximating the height of a human disc space and a length approaching the sagittal diameter of the vertebral body, said capsule comprising:
    a flexible bladder which
        is chemically and biologically inert, and which comprises a semi-permeable membrane,
        enclosing a fluid containing a therapeutic material that is slowly diffusible thrugh the semi-permeable membrane, and
        through which the therapeutic material is slowly diffusible but through which cells will not pass, and said capsule further comprising
    a layer of strong fibers encompassing the fluid-filled membrane.

* * * * *